United States Patent
Hirayama et al.

(10) Patent No.: US 11,684,556 B2
(45) Date of Patent: Jun. 27, 2023

(54) CLEANER COMPOSITION

(71) Applicant: SHISEIDO COMPANY, LTD., Tokyo (JP)

(72) Inventors: Natsumi Hirayama, Kanagawa (JP); Sayoko Kawano, Kanagawa (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 151 days.

(21) Appl. No.: 16/644,012

(22) PCT Filed: Sep. 14, 2018

(86) PCT No.: PCT/JP2018/034108
§ 371 (c)(1),
(2) Date: Mar. 3, 2020

(87) PCT Pub. No.: WO2019/059111
PCT Pub. Date: Mar. 28, 2019

(65) Prior Publication Data
US 2021/0000716 A1    Jan. 7, 2021

(30) Foreign Application Priority Data
Sep. 19, 2017 (JP) .................. 2017-178605

(51) Int. Cl.
*A61K 8/00* (2006.01)
*A61K 8/36* (2006.01)
*A61K 8/04* (2006.01)
*A61K 8/81* (2006.01)
*A61Q 19/10* (2006.01)

(52) U.S. Cl.
CPC .............. *A61K 8/36* (2013.01); *A61K 8/046* (2013.01); *A61K 8/817* (2013.01); *A61K 8/8158* (2013.01); *A61Q 19/10* (2013.01); *A61K 2800/5426* (2013.01); *A61K 2800/87* (2013.01)

(58) Field of Classification Search
CPC ......... A61K 8/36; A61K 8/8158; A61K 8/817
See application file for complete search history.

(56) References Cited

U.S. PATENT DOCUMENTS

| | | | | |
|---|---|---|---|---|
| 8,034,755 B2* | 10/2011 | Kawano | ................ | A61Q 19/00 510/136 |
| 8,394,360 B2* | 3/2013 | Kato | ................ | A61K 8/731 424/70.13 |
| 8,946,137 B2* | 2/2015 | Kimura | ................ | A61K 8/42 510/130 |
| 2006/0094610 A1* | 5/2006 | Yamato | ................ | A61K 8/361 510/130 |
| 2006/0135397 A1* | 6/2006 | Bissey-Beugras | ... | C11D 3/3765 510/475 |
| 2014/0086864 A1* | 3/2014 | Ishimori | ................ | A61K 8/87 424/70.122 |
| 2020/0148980 A1* | 5/2020 | Cheng | ................ | C11D 17/006 |

FOREIGN PATENT DOCUMENTS

| | | |
|---|---|---|
| CN | 104394837 A | 3/2015 |
| CN | 104394837 B | 12/2016 |
| JP | 9-157688 A2 | 6/1997 |
| JP | 2017-88555 A | 5/2017 |
| JP | 6287835 B2 | 3/2018 |
| KR | 20150035557 A | 4/2015 |
| PH | 12014502877 A1 | 2/2015 |
| WO | 2014/003114 A1 | 1/2014 |

OTHER PUBLICATIONS

SHISEIDO, Japan, Cleansing Soap, Mintel GNPD, Dec. 2015, ID: 3673929; Cited in ISR.
FT SHISEIDO, Japan, Speedy Perfect Whip, Mintel GNPD, Aug. 2018, ID: 5888113; Cited in ISR.
International Search Report (ISR) issued in PCT/JP2018/034108 dated Dec. 18, 2018.
"Cleansing Soap", SHISEIDO, Mintel GNPD, Dec. 31, 2015, pp. 1-4; Concise explanation of the relevance is included in he CN Office Action.
Chinese Office Action dated Jul. 11, 2022 for Chinese Patent Application No. 201880058428.8; English machine translation.

* cited by examiner

*Primary Examiner* — Necholus Ogden, Jr.
(74) *Attorney, Agent, or Firm* — Rankin, Hill & Clark LLP

(57) ABSTRACT

Provided is a cleaner composition which causes no malfunction due to clogging even when contained in a pump foamer container, or the like, and repeatedly used, and is excellent in resilience and persistence of foam, and feeling after washing off. The cleaner composition includes a soap that is obtained by neutralizing a higher fatty acid with sodium N-methyltaurate, and a polymer including dimethyl diallyl ammonium chloride as a monomer unit and having a molecular weight of 200000 or less.

4 Claims, No Drawings

CLEANER COMPOSITION

TECHNICAL FIELD

The present invention relates to a cleaner composition to be contained in a pump foamer container that internally includes a porous film and discharges the contents in a foam with air, or in an aerosol container that ejects the contents in a foam with a liquefied gas through a narrow passage, the cleaner composition causing no clogging in the porous film or the passage even when repeatedly used, and being excellent in persistence, resilience, and ease of washing off of foam.

BACKGROUND ART

In order to wash off makeup or the like with ease, a cleaner product that includes a cleaner contained in a pump foamer container or an aerosol container and ejects the cleaner in a foam is known.

With such a cleaner product, the ejected foam is required to be applied and spread over the entire face, and hence the foam is required to have appropriate resilience and persistence. In order to impart appropriate resilience and persistence to the foam, it is effective to include a cation polymer in the cleaner. However, when the molecular weight of the cation polymer is too large, clogging becomes likely to be caused in the porous film or the passage, which may make it impossible to eject the cleaner.

Further, the cleaner includes, as a cleaning component, a soap that is obtained by subjecting a higher fatty acid to a neutralization treatment. However, according to the kind of the neutralizing agent for use in the neutralization treatment, even when a cation polymer is included, sufficient resilience of the foam cannot be obtained. Accordingly, the feeling after washing off is also not satisfactory.

Therefore, in order to develop a cleaner composition that causes no clogging in a pump foamer container or the like even when repeatedly used, and is excellent in resilience and persistence of foam, and feeling after washing off, it is important to conduct studies on appropriate cation polymers, and neutralizing agents for subjecting a higher fatty acid to a neutralization treatment.

CITATION LIST

Patent Literature

[PTL 1] Japanese Patent Application Publication No. 2017-88555

SUMMARY OF INVENTION

Technical Problem

It is an object of the present invention to provide a cleaner composition which causes no malfunction due to clogging even when contained in a pump foamer container or the like, and repeatedly used, and is excellent in resilience and persistence of foam, and feeling after washing off.

Solution to Problem

In order to solve the problem, the present inventors conducted studies. As a result, the present inventors found that including a soap that is obtained by neutralizing a higher fatty acid with sodium N-methyltaurate, and a polymer including dimethyl diallyl ammonium chloride as a monomer unit and having a molecular weight of 200000, or less can provide a cleaner that is repeatedly usable by a pump foamer container, or the like, and is furthermore rich in persistence and resilience of foam, and also excellent in feeling after washing off. This led to the completion of the present invention.

Namely, the present invention relates to a cleaner composition, including:
a soap that is obtained by neutralizing a higher fatty acid with sodium N-methyltaurate; and
a polymer including dimethyl diallyl ammonium chloride as a monomer unit and having a molecular weight of 200000 or less.

Advantageous Effect of Invention

In accordance with the cleaner composition of the present invention, it is possible to obtain a cleaner that is capable of repeated use by a pump foamer container, or the like, and is furthermore rich in resilience and persistence of foam, and also excellent in feeling after washing off.

DESCRIPTION OF EMBODIMENTS

A cleaner composition of the present invention is characterized by including a soap that is obtained by neutralizing a higher fatty acid with sodium N-methyltaurate, and a polymer including dimethyl diallyl ammonium chloride as a monomer unit and having a molecular weight of 200000 or less.

The higher fatty acid for use in the present invention is a straight-chain or branched saturated or unsaturated fatty acid having about 5 to 25 carbon atoms. Examples thereof may include caproic acid, heptanoic acid, caprylic acid, pelargonic acid, capric acid, undecanoic acid, lauric acid, caproleic acid, undecylenic acid, lauroleic acid, 2-ethyl butanoic acid, isopentanoic acid, 2-ethylpentanoic acid, 2-ethylhexanoic acid, isononanoic acid, 3,5,5-trimethylhexanoic acid, tridecanoic acid, tetramethylnonanoic acid, myristic acid, pentadecanoic acid, palmitic acid, stearic acid, arachic acid, behenic acid, lignoceric acid, cerotic acid, myristoleic acid, palmitoleic acid, oleic acid, elaidic acid, gondoic acid, erucic acid, selacholeic acid, linoleic acid, linoelaidic acid, linolenic acid, arachidonic acid, 2-hexyldecanoic acid, isostearic acid, 12-hydroxystearic acid, coconut oil fatty acid, hardened coconut oil fatty acid, palm oil fatty acid, hardened palm oil fatty acid, palm kernel oil fatty acid, hardened palm kernel oil fatty acid, beef tallow fatty acid, and hardened beef tallow fatty acid. Out of these, straight-chain saturated fatty acids having 12 to 18 carbon atoms such as lauric acid, myristic acid, palmitic acid, and stearic acid are preferable.

As the neutralizing agent for subjecting a higher fatty acid to a neutralization treatment, sodium N-methyltaurate is used. The neutralization rate is preferably 100% to 150%. When the neutralization rate is smaller than 100%, the crystal of a higher fatty acid is precipitated at lower temperatures. This may cause clogging in the porous film of a pump foamer, or the like. On the other hand, when the neutralization rate exceeds 150%, the cleaner may undesirably be discolored over time, or may undergo other problems. For the neutralization treatment, sodium N-methyltaurate is placed in a reaction container, and is heated to about 60° C. (degree Celsius), and a mixed fatty acid is added thereto for neutralization, thereby forming a soap.

Examples of the polymer including dimethyl diallyl ammonium chloride as a monomer unit for use in the present invention may include a dimethyl diallyl ammonium chloride/acrylic acid copolymer, a dimethyl diallyl ammonium chloride/acrylamide/acrylic acid copolymer, and a dimethyl diallyl ammonium chloride/acrylamide copolymer.

Further, the molecular weight of the polymer including dimethyl diallyl ammonium chloride as a monomer unit is set as 200000 or less. When the molecular weight exceeds 200000, an impermissible flow resistance may be caused in a porous film included in a pump foamer or a small passage of an aerosol container. This may entail a malfunction of the pump foamer container, or the like due to clogging. For this reason, in order to obtain a foam having an appropriate resilience while enabling ejection of a foam due to repetition, the molecular weight of the polymer is required to be adjusted to 200000 or less. Incidentally, the commercially available products of such a dimethyl allyl ammonium chloride-acrylamide copolymer (molecular weight 120000) include "Merquat 740" (corresponding to "Polyquaternium-7" in cosmetic ingredient labeling), a product manufactured by The Lubrizol Corporation, and the like. The commercially available products of acrylamide-acrylic acid-dimethyl diallyl ammonium chloride copolymer (molecular weight 150000) include "Merquat 3940" (corresponding to "Polyquaternium-39" in cosmetic ingredient labeling), a product manufactured by The Lubrizol Corporation, and the like.

In the cleaner composition of the present invention, in addition to the essential components described above, one or two or more of other components commonly included in cosmetic and pharmaceutical products can be included within the range not to impair the effects of the present invention. Specific examples thereof will be shown below. However, the present invention is not limited thereto.

As a moisturizer, polyethylene glycol, glycerin, propylene glycol, dipropylene glycol, butylene glycol, isoprene glycol, sorbitol, xylitol, maltitol, mucopolysaccharide, hyaluronic acid, chondroitin sulfuric acid, chitosan, or the like can be included. As a thickener, methyl cellulose, ethyl cellulose, gum arabic, polyvinyl alcohol, montmorillonite, laponite, or the like can be included. Further, as a solvent, ethanol or the like can be included.

As an antioxidant, butyl hydroxy toluene, tocopherol, phytic acid, or the like can be added, and as the antibacterial antiseptic agent, benzoic acid, salicylic acid, sorbic acid, paraoxy benzoic acid alkyl ester (such as ethyl paraben or butyl paraben), hexachlorophene, or the like can be included.

As a surfactant, nonionic surfactants such as polyethylene glycol diisostearate, polyethylene glycol monoisostearate, polyoxyethylene glyceryl isostearate, polyoxyethylene glyceryl triisostearate, sorbitan monolaurate, sorbitan monopalmitate, sorbitan sesquioleate, sorbitan trioleate, polyoxyethylene sorbitan monolaurate, polyethylene glycol monooleate, polyoxyethylene alkyl ether, polyglycol diester, lauroyl diethanolamide, fatty acid isopropanol amide, maltitol hydroxy aliphatic ether, alkylated polysaccharide, alkyl glucoside, sugar ester, and polyoxyethylene/methyl polysiloxane copolymer, cationic surfactants such as stearyl trimethyl ammonium chloride, benzalkonium chloride, and lauryl amine oxide, anionic surfactants such as sodium palmitate, sodium laurate, sodium lauryl sulfate, potassium laurate, triethanolamine polyoxyethylene alkyl sulfate, turkey-red oil, linear dodecyl benzenesulfuric acid salt, polyoxyethylene hardened castor oil maleic acid, arginine cocoate, and acyl methyl taurine salt, and amphoteric surfactants such as coconut oil fatty acid hydroxypropyl betaine and lauryl betaine can be included.

As other components, a pigment, a fragrance, a stabilizer, and the like can be appropriately included.

The cleaner composition of the present invention is preferably provided in a form of facial cleanser, body soap, hand soap, shampoo, or the like as a cleaner for hair or skin contained in a pump foamer container, or the like.

EXAMPLES

The present invention will be described below in more details by way of examples. However, the examples is not intended to restrict the present invention. Note that each numerical value in tables represents the numerical value in terms of mass % unless otherwise specified.

A cleaner was routinely prepared with the composition described in each example in the tables below. The prepared cleaner was contained in a pump foamer container having porous films. A pump mechanism is included in the pump foamer container. When the upper surface of a cap connected with the pump mechanism is pressed with a finger, the cleaner composition contained in the container is mixed with air and passes through the porous films (two pieces of 200 mesh and 305 mesh) to be discharged in a foam from a container discharge port.

The cleaner discharged from the pump foamer container was evaluated in eight grades in terms of four items of "fineness of foam upon discharging", "resilience of foam", "ease of washing off", and "moist feeling after washing off" by a special panel. Note that 4 to 8 of 8 grades are judged as acceptable, and 1 to 3 are judged as unacceptable.

TABLE 1

| Classification | Component name | Comp. Ex. 1 | Ex. 1 | Ex. 2 | Ex. 3 | Ex. 4 | Ex. 5 | Comp. Ex. 2 | Ex. 6 |
|---|---|---|---|---|---|---|---|---|---|
| | Water | to 100 | to 100 | to 100 | to 100 | to 100 | to 100 | to 100 | to 100 |
| Moisturizer | Glycerin | 10 | 10 | 10 | 10 | 10 | 10 | 10 | 10 |
| | DPG | 5 | 5 | 5 | 5 | 5 | 5 | 5 | 5 |
| | BG | 5 | 5 | 5 | 5 | 5 | 5 | 5 | 5 |
| | Sorbitol | 15 | 15 | 15 | 15 | 15 | 15 | 15 | 15 |
| | Arginine cocoate | 1 | 1 | 1 | 1 | 1 | 1 | 1 | 1 |
| | Lauryl betaine | 4 | 4 | 4 | 4 | 4 | 4 | 4 | 4 |
| Higher fatty acid | Lauric acid | 4 | 4 | 4 | 4 | 4 | 4 | 4 | 4 |
| | Myristic acid | 1 | 1 | 1 | 1 | 1 | 1 | 1 | 1 |
| Neutralizing agent | Sodium N-methyltaurate | 4 | 4 | 4 | 4 | 4 | 4 | 4 | 4 |
| Cation polymer | Polyquaternium-7 (molecular weight 120000) *1 | — | 0.01 | 0.05 | 0.5 | 1 | 3 | 5 | — |

TABLE 1-continued

| Classification | Component name | | | | | | | | |
|---|---|---|---|---|---|---|---|---|---|
| | Polyquaternium-39 (molecular weight 150000) *2 | — | — | — | — | — | — | — | 0.01 |
| | Polyquaternium-7 (molecular weight 1600000) *3 | — | — | — | — | — | — | — | — |
| | Stabilizer | Proper amount | Proper amount | Proper amount | Proper amount | Proper amount | Proper amount | Proper amount | Proper amount |
| | Fragrance | Proper amount | Proper amount | Proper amount | Proper amount | Proper amount | Proper amount | Proper amount | Proper amount |
| | Total | 100 | 100 | 100 | 100 | 100 | 100 | 100 | 100 |
| Usability | Fineness of foam upon discharging (appearance) | 6 | 6 | 6 | 6 | 5 | 4 | 2 | 6 |
| | Foam resilience | 3 | 4 | 5 | 7 | 8 | 7 | 6 | 4 |
| | Ease of washing off | 6 | 6 | 6 | 6 | 4 | 4 | 2 | 6 |
| | Moist feeling after washing off | 2 | 4 | 5 | 6 | 7 | 7 | 8 | 4 |

| | Classification | Component name | Ex. 7 | Ex. 8 | Ex. 9 | Ex. 10 | Comp. Ex. 3 | Comp. Ex. 4 |
|---|---|---|---|---|---|---|---|---|
| | Moisturizer | Water | to 100 | to 100 | to 100 | to 100 | to 100 | to 100 |
| | | Glycerin | 10 | 10 | 10 | 10 | 10 | 10 |
| | | DPG | 5 | 5 | 5 | 5 | 5 | 5 |
| | | BG | 5 | 5 | 5 | 5 | 5 | 5 |
| | | Sorbitol | 15 | 15 | 15 | 15 | 15 | 15 |
| | | Arginine cocoate | 1 | 1 | 1 | 1 | 1 | 1 |
| | | Lauryl betaine | 4 | 4 | 4 | 4 | 4 | 4 |
| | Higher fatty acid | Lauric acid | 4 | 4 | 4 | 4 | 4 | 4 |
| | | Myristic acid | 1 | 1 | 1 | 1 | 1 | 1 |
| | Neutralizing agent | Sodium N-methyltaurate | 4 | 4 | 4 | 4 | 4 | 4 |
| | Cation polymer | Polyquaternium-7 (molecular weight 120000) *1 | — | — | — | — | — | — |
| | | Polyquaternium-39 (molecular weight 150000) *2 | 0.05 | 0.5 | 1 | 2 | 5 | — |
| | | Polyquaternium-7 (molecular weight 1600000) *3 | — | — | — | — | — | 1 |
| | | Stabilizer | Proper amount | Proper amount | Proper amount | Proper amount | Proper amount | Proper amount |
| | | Fragrance | Proper amount | Proper amount | Proper amount | Proper amount | Proper amount | Proper amount |
| | | Total | 100 | 100 | 100 | 100 | 100 | 100 |
| | Usability | Fineness of foam upon discharging (appearance) | 6 | 6 | 5 | 4 | 2 | *Note |
| | | Foam resilience | 5 | 6 | 7 | 6 | 5 | *Note |
| | | Ease of washing off | 6 | 6 | 6 | 5 | 4 | *Note |
| | | Moist feeling after washing off | 5 | 5 | 6 | 6 | 8 | *Note |

*Note:
Not evaluable
*1 "Merquat 740", a product manufactured by The Lubrizol Corporation (dimethyl allyl ammonium chloride-acrylamide copolymer (molecular weight 120000) INCI name: Polyquaternium-7)
*2 "Merquat 3940", a product manufactured by The Lubrizol Corporation (acrylamide-acrylic acid-dimethyl allyl ammonium chloride copolymer (molecular weight 150000) INCI name: Polyquaternium-39)
*3 "Merquat 550", a product manufactured by The Lubrizol Corporation (dimethyl allyl ammonium chloride-acrylamide copolymer (molecular weight 1600000) INCI name: Polyquaternium-7)

Table 1 shows the results of the studies on the kind and the amount of the cation polymer to be included in the cleaner. As for Examples 1 to 5 each including Polyquaternium-7 (dimethyl diallyl ammonium chloride-acrylamide copolymer) with a molecular weight of 120000 in an amount of 0.01% to 3%, and Examples 6 to 10 each including Polyquaternium-39 (acrylamide-acrylic acid-dimethyl diallyl ammonium chloride copolymer) with a molecular weight of 150000 in an amount of 0.01% to 2%, good results could be confirmed in all the evaluation items. Note that Comparative Example 4 including Polyquaternium-7 (dimethyl diallyl ammonium chloride-acrylamide copolymer) with a molecular weight of 1600000 could not be evaluated due to an impermissible flow resistance that caused malfunction of the pump foamer container.

TABLE 2

| Classification | Component name | Comp. Ex. 5 | Comp. Ex. 6 | Comp. Ex. 7 | Ex. 11 |
| --- | --- | --- | --- | --- | --- |
| | Water | to 100 | to 100 | to 100 | to 100 |
| Moisturizer | Glycerin | 10 | 10 | 10 | 10 |
| | DPG | 5 | 5 | 5 | 5 |
| | BG | 5 | 5 | 5 | 5 |
| | Sorbitol | 15 | 15 | 15 | 15 |
| Higher fatty acid | Lauric acid | 4 | 4 | 4 | 4 |
| | Myristic acid | 1 | 1 | 1 | 1 |
| Neutralizing agent | Sodium N-methyltaurate | — | — | 4 | 4 |
| | Potassium hydroxide | 1.5 | 1.5 | — | — |
| Cation polymer | Polyquaternium-7 (molecular weight 120000) *1 | — | 1 | — | 1 |
| | Stabilizer | Proper amount | Proper amount | Proper amount | Proper amount |
| | Fragrance | Proper amount | Proper amount | Proper amount | Proper amount |
| | Total | 100 | 100 | 100 | 100 |
| Usability | Fineness of foam upon discharging (appearance) | 6 | 6 | 6 | 6 |
| | Foam resilience | 1 | 2 | 2 | 7 |
| | Ease of washing off | 8 | 6 | 6 | 6 |
| | Moist feeling after washing off | 1 | 2 | 2 | 7 |

*1 "Merquat 740", a product manufactured by The Lubrizol Corporation (dimethyl allyl ammonium chloride-acrylamide copolymer (molecular weight 120000) INCI name: Polyquaternium-7)

Table 2 shows the results of the studies on the combination of a neutralizing agent for neutralizing a higher fatty acid and a cation polymer. When potassium hydroxide was used as the neutralizing agent, the following results were observed: the resilience of foam was insufficient, and the moist feeling after washing off was also inferior (Comparative Examples 5 and 6). As for Example 11 in which sodium N-methyltaurate was included as the neutralizing agent, and Polyquarternium-7 (dimethyl diallyl ammonium chloride-acrylamide copolymer) with a molecular weight of 120000 was included as the cation polymer, good results could be obtained in terms of all the items.

The invention claimed is:

1. A cleaner composition contained in a pump foamer container, comprising:
   a higher fatty acid;
   sodium N-methyltaurate; and
   0.01 mass % to 3 mass % with respect to a total amount of the cleaner composition of a polymer including dimethyl allyl ammonium chloride-acrylamide copolymer or acrylamide-acrylic acid-dimethyl diallyl ammonium chloride copolymer and having a molecular weight of 150000 or less.

2. The cleaner composition contained in a pump foamer container of claim 1, wherein
   the higher fatty acid is neutralized by the sodium N-methyltaurate with a neutralization rate of 100% to 150%.

3. A pump foamer container containing a cleaner composition, the cleaner composition comprising:
   a higher fatty acid;
   sodium N-methyltaurate; and
   0.01 mass % to 3 mass % with respect to a total amount of the cleaner composition of a polymer including dimethyl allyl ammonium chloride-acrylamide copolymer or acrylamide-acrylic acid-dimethyl diallyl ammonium chloride copolymer and having a molecular weight of 150000 or less.

4. The cleaner composition contained in a pump foamer container of claim 1, wherein the polymer includes dimethyl allyl ammonium chloride-acrylamide copolymer.

* * * * *